US007544860B2

(12) United States Patent
Lightner et al.

(10) Patent No.: US 7,544,860 B2
(45) Date of Patent: Jun. 9, 2009

(54) GENERATION OF PLANTS WITH ALTERED OIL CONTENT

(75) Inventors: Jonathan Lightner, Des Moines, IA (US); Hein Tsoeng Ng, Charlottesville, VA (US)

(73) Assignee: Agrinomics, LLC, Portland, OR (US)

( * ) Notice: Subject to any disclaimer, the term of this patent is extended or adjusted under 35 U.S.C. 154(b) by 105 days.

(21) Appl. No.: 10/553,884

(22) PCT Filed: Apr. 19, 2004

(86) PCT No.: PCT/US2004/012278

§ 371 (c)(1), (2), (4) Date: Jun. 19, 2006

(87) PCT Pub. No.: WO2004/093531

PCT Pub. Date: Nov. 4, 2004

(65) Prior Publication Data

US 2006/0277630 A1 Dec. 7, 2006

Related U.S. Application Data

(60) Provisional application No. 60/464,558, filed on Apr. 22, 2003.

(51) Int. Cl.
*A01H 5/00* (2006.01)
*C12N 15/82* (2006.01)

(52) U.S. Cl. ........................................ 800/298; 800/281
(58) Field of Classification Search ........................ None
See application file for complete search history.

(56) References Cited

U.S. PATENT DOCUMENTS

| 5,639,790 A | 6/1997 | Voelker et al. |
| 5,704,160 A | 1/1998 | Bergquist et al. |
| 6,229,033 B1 | 5/2001 | Knowlton |
| 6,248,939 B1 | 6/2001 | Leto et al. |
| 6,372,965 B1 | 4/2002 | Lightner et al. |

OTHER PUBLICATIONS

Doerks et al, TIG 14(6): 248-250, Jun. 1998.*
Brenner, S.E., TIG 15(4): 132-133, Apr. 1999.*
Bork et al, TIG 12(10): 425-427, Oct. 1996.*
Broun et al, Science 282: 1315-1317, Nov. 13, 1998.*
Eccleston and Ohlrogge, "Expressions of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.

Feldmann et al., "A Dwarf Mutant of *Arabidopsis* Generated by T-DNA Insertion Mutagenesis," *Science*, 243(4896):1351-1354, 1989.
Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.
Girke et al., "Microarray analysis of developing *Arabidopsis* seeds," *Plant Physiol.*, 124:1570-1581, 2000.
Jako et al., "Seed-specific over-expression of an *Arabidopsis* cDNA encoding a diacylglycerol acyltransferase enhances seed oil content and seed weight," *Plant Physiol.*, 126(2):861-874, 2001.
James and Dooner, "Isolation of EMS-induced mutants in *Arabidopsis* altered in seed fatty acid composition," *Theor. Appl. Genet.*, 80(2):241-245, 1990.
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Larson et al., "Acyl CoA profiles of transgenic plants that accumulate medium-chain fatty acids indicate inefficient storage lipid synthesis in developing oilseeds," *Plant J.*, 32:519-527, 2002.
Lemieux et al., "Mutants of *Arabidopsis* with alterations in seed lipid fatty acid composition," *Theor. Appl. Genet.*, 80(2):234-240, 1990.
Lin et al., "The Pex16p homolog SSE1 and storage organelle formation in *Arabidopsis* seeds," *Science.* 284:328-330, 1999.
Lionneton et al., "Development of an AFLP-based linkage map and localization of QTLs for seed fatty acid content in condiment mustard (*Brassica juncea*)," *Genome*, 45(6):1203-1215, 2002.
Liu and Butow, "A transcriptional switch in the expression of yeast tricarboxylic acid cycle genes in response to a reduction or loss of respiratory function," *Mol. Cell. Biol.*, 19:6720-6728, 1999.
McCallum et al., "Targeted screening for induced mutations," *Nat. Biotechnol.*, 18(4):455-457, 2000.
Mekhedov et al., "Toward a functional catalog of the plant genome. A survey of genes for lipid biosynthesis," *Plant Physiol.*, 122:389-401, 2000.
Moire et al., "Impact of unusual fatty acid synthesis on futile cycling through β-oxidation and on gene expression in transgenic plants," *Plant Physiol.*, 134:432-442, 2004.
Neuhaus and Emes, "Nonphotosynthetic Metabolism In Plastids," *Annu. Rev. Plant Physiol. Plant Mol. Biol.*, 51:111-140, 2000.
O'Hara et al., "Fatty acid and lipid biosynthetic genes are expressed at constant molar ratios but different absolute levels during embryogenesis," *Plant Physiol.*, 129:310-320, 2002.
Okuley et al., "*Arabidopsis* FAD2 Gene Encodes the Enzyme That Is Essential for Polyunsaturated Lipid Synthesis," *Plant Cell*, 6:147-158, 1994.
Pritchard et al., "Germination and storage reserve mobilization are regulated independently in *Arabidopsis*," *Plant J.*, 31(5):639-647, 2002.

(Continued)

*Primary Examiner*—Elizabeth F McElwain
(74) *Attorney, Agent, or Firm*—Klarquist Sparkman, LLP

(57) ABSTRACT

The present invention is directed to plants that display an altered oil content phenotype due to altered expression of a HIO103.1 nucleic acid. The invention is further directed to methods of generating plants with an altered oil content phenotype.

14 Claims, No Drawings

OTHER PUBLICATIONS

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during *Arabidopsis* seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of a acyl-CoA synthetase from *Arabidopsis thaliana*," *Biochem Soc. Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Wada et al., "Role of a positive regulator of root hair development, CAPRICE, in *Arabidopsis* root epidermal cell differentiation," *Development*, 129(23):5409-5419, 2002.

White et al., "A new set of *Arabidopsis* expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

Anoop et al., "Modulation of citrate metabolism alters aluminum tolerance in yeast and transgenic canola overexpressing a mitochondrial citrate synthase," *Plant Physiol.*, 132:2205-2217, 2003.

Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.

Colbert et al., "High-throughput screening for induced point mutations," *Plant Physiol.*, 126(2):480-484, 2001.

Dehesh et al., "Overexpression of 3-ketoacyl-acyl-carrier protein synthase IIIs in plants reduces the rate of lipid synthesis," *Plant Physiol.*, 125:1103-1114, 2001.

Eastmond and Graham, "Re-examining the role of glyoxylate cycle in oilseeds," *Trends Plant Sci.*, 6(2):72-77, 2001.

\* cited by examiner

SEQUENCE LISTING

<160> NUMBER OF SEQ ID NOS: 6

<210> SEQ ID NO 1
<211> LENGTH: 693
<212> TYPE: DNA
<213> ORGANISM: Arabidopsis thaliana

<400> SEQUENCE: 1

```
atgccaaaca ctagcagctc tcaaagcttc actatcttcg ttgatggttg gttaatccgt      60
cacaggtatt tcgttgaaca gcttatgtgt gcttcttcct tggatgaaac taatcgtatc     120
tctctcgaag aacaacaatc tctcgtggcc cagtttctat ctcactgtct tcaatactac     180
caagagaaat tcgcctccgt ttccctcgcc ggggacaacg ttttcacttt cttctgccca     240
ccgtggttta actcctacgc taaacttatt ttatgggtcg gcgatttcaa gccttctctt     300
gtgtttaaac tcaccgaggt ctccgtggcc gacctcacgc gccaccagaa agaccggatc     360
tcgagtctta agtcggagac taggaggaaa gagagagaag ttatgcgaga tttcgccctc     420
gtgcaacaaa gcgtggcgga tccgccggtg atgctcgcgg cgaggcgcgt gggagcggtg     480
ggaatggtgg acggagaaga aacggatttg gaggaggcga tggaggtgct aaagctggg      540
atggcggcag cgatgaacaa cgctgatcag ctacggtgtt cgacggtggg aaagtggtg      600
gagattctta ctccgccgca agcgattaaa gtgttgagga caatcggaca gcttcacctc     660
cgtctgagag acagagacca agaaagagct taa                                  693
```

<210> SEQ ID NO 2
<211> LENGTH: 230
<212> TYPE: PRT
<213> ORGANISM: Arabidopsis thaliana

<400> SEQUENCE: 2

```
Met Pro Asn Thr Ser Ser Gln Ser Phe Thr Ile Phe Val Asp Gly
  1               5                  10                  15

Trp Leu Ile Arg His Arg Tyr Phe Val Glu Gln Leu Met Cys Ala Ser
                 20                  25                  30

Ser Leu Asp Glu Thr Asn Arg Ile Ser Leu Glu Glu Gln Gln Ser Leu
         35                  40                  45

Val Ala Gln Phe Leu Ser His Cys Leu Gln Tyr Tyr Gln Glu Lys Phe
     50                  55                  60

Ala Ser Val Ser Leu Ala Gly Asp Asn Val Phe Thr Phe Phe Cys Pro
 65                  70                  75                  80

Pro Trp Phe Asn Ser Tyr Ala Lys Leu Ile Leu Trp Val Gly Asp Phe
                 85                  90                  95

Lys Pro Ser Leu Val Phe Lys Leu Thr Glu Val Ser Val Ala Asp Leu
            100                 105                 110

Thr Arg His Gln Lys Asp Arg Ile Ser Ser Leu Lys Ser Glu Thr Arg
        115                 120                 125

Arg Lys Glu Arg Glu Val Met Arg Asp Phe Ala Leu Val Gln Gln Ser
    130                 135                 140

Val Ala Asp Pro Pro Val Met Leu Ala Ala Arg Arg Val Gly Ala Val
145                 150                 155                 160

Gly Met Val Asp Gly Glu Glu Thr Asp Leu Glu Glu Ala Met Glu Val
                165                 170                 175

Leu Lys Ala Gly Met Ala Ala Met Asn Asn Ala Asp Gln Leu Arg
            180                 185                 190
```

Cys Ser Thr Val Gly Lys Val Val Glu Ile Leu Thr Pro Pro Gln Ala
        195                 200                 205

Ile Lys Val Leu Arg Thr Ile Gly Gln Leu His Leu Arg Leu Arg Asp
    210                 215                 220

Arg Asp Gln Glu Arg Ala
225                 230

<210> SEQ ID NO 3
<211> LENGTH: 1163
<212> TYPE: DNA
<213> ORGANISM: Arabidopsis thaliana

<400> SEQUENCE: 3

| | | | |
|---|---|---|---|
| gagaactggg gagagtcagc tatggctggt agccctatga ctgacacatc tacagatcca | 60 |
| gacactgatg agaggaacca gatgtttgaa caaggacttg ttgctgtccc cacagcttct | 120 |
| gattctagtg acaaatcaag ggacaaacta gatcagaaga cacttcggcg tcttgcccaa | 180 |
| aatcgtgaag ctgcccggaa aagccgttta cgaaagaagg catacatcca aaaccttgag | 240 |
| agtagcagat tgaaacttac tcagttagag caagagcttc accagactcg tcaacagggt | 300 |
| atttttattt ctacatcagg agatcaacct caatcaacaa gcggaaatgg agctttggca | 360 |
| tttgacatgg agtatgcacg ctggttggaa gagcacaaca acatgtaaa tgagttgagg | 420 |
| cttgcagtca atgcacatgc cggtgataat gatctccgtg gtattgttgg tagtgttatg | 480 |
| gcacactacg atgaattttt caggctcaag gtgtggcag ctagatcaga tgttttttcat | 540 |
| gtgctgtctg gatgtggaa gaccctgct gagagatgtt tcatgtggtt aggtggcttc | 600 |
| cgatcatctg aggttcttaa gttactggca ggtcacctag agcctcttac tgatcagcag | 660 |
| cttgttggta tatccaacct gcagcagtcc tcccaacaag ctgaagatgc tcttctcaa | 720 |
| gggatggaag cattacaaca gtcgcttgca gaaactctag catctggatc cctgggccct | 780 |
| gctggacctt ctggcaatgt tgcaaattac atgggacaaa tggcgatggc tatgggaaaa | 840 |
| cttggcaccc tagagaactt tctacgacag gctgataatc tacggctgca aacacttcaa | 900 |
| caaatgcaac gcatcttaac caccccgacaa tccgcacgag ccctacttgc aataagcgac | 960 |
| tacttctctc ggctgcgtgc tttgagttct ctttggcttg cccgtccaag ggaataaatt | 1020 |
| caattaactc ataaatagga ttttttttgt actgtctcta gtatgtcaat tagtttcttc | 1080 |
| acattgctca tgtgttgatg ggatatttgg atctaagatc ttatgaatgg atgacatgta | 1140 |
| tgtgttcaag tgaaaaaaaa aaa | 1163 |

<210> SEQ ID NO 4
<211> LENGTH: 1024
<212> TYPE: DNA
<213> ORGANISM: Arabidopsis thaliana
<220> FEATURE:
<221> NAME/KEY: misc_feature
<222> LOCATION: (416)..(417)
<223> OTHER INFORMATION: n is a, c, g, or t

<400> SEQUENCE: 4

| | | | |
|---|---|---|---|
| tggaaagaac cttttttttgg gttgggggggt tcaaacctgg aatggccttt caggttgtga | 60 |
| acgcagcttt ggaggttttg tcagaacagc aaaaggagag gctgagtttg ctcaaccaag | 120 |
| agaccaaggt gaaggagaga gccctcaatg atgagttggc caagcttcat gagagtgtgg | 180 |
| cagctccacc gctggtggac atggccagga gccatggtag ggtgtgtttc agtaggtcct | 240 |
| tcatggcaga tggggggttct tccgttccaa gcactttcag atagacattg gagaatctgg | 300 |

```
aggcaaatgc agatgctttg aggacaaaca catctttgaa gattctccag atactgagac      360
cttctcagct tgtttcattc ttggctgctg tggctgagct tcagatcagg attggnncctt    420 ggggtttgga caaggatgcc ctgaatggag gccaagggtg aaagtcaatt aacgggaatt     480
tgaaggcttt tttatgtaag ttgctttcag ttttttgtctt ttttgggaac tggtttgagt    540
tggaggatgg atacataggc atttagcctt ttagcatcat gatgatggat ggtgtgcatt     600
gggcagtgag catgttcact gcctgtaatg ttgtttctct ctacctggtt tggtgggcat     660
tgaacaatga tgaacaaaac aaggccatgc aatgcatact tttatctaga ggctaaaagc     720
atcaatatat ttgtacctct tgagatagag gcaagtactc caggttctct ctactcaagc     780
agctacccca gatttcaatt ggttgctata tttaccatag taagtaggta gtagatacct     840
aaggattatt tattttttctt tttttttgtga tattaagaca tgtttttctaa tttctagtga  900 agaacttgga tggatgtata ggatgtggta ccttgaaaat tacttttcaa cgtcccactc     960
actttgacat tgcatcaaag taagtttctc cctaaggggt cttttttggtc ctttcctcaa   1020 caca                                                                 1024

<210> SEQ ID NO 5
<211> LENGTH: 1234
<212> TYPE: DNA
<213> ORGANISM: Arabidopsis thaliana

<400> SEQUENCE: 5
ggcgcatgct gcaggtgcaa ctgagcaatt gcagacctgg gagttgcttc cattatcttg      60
cacacactac taggtggcta gccatcgagc acaatcatgt ccaagctggc aagtagtgct     120
tcataccttg tctccacctc gccaaacggt tctccttccc gtgaaacgtt tcgcaaattc     180
ttcgagtgct ggcttggaga gcaaaacaat tatctcgaac aactcatctc aacctgtaaa     240
gattatgatc acaacagaaa aaactccccc cagtcatctc aggcaaccct ccagcctctt     300
atcaaccgtg ttcttgagca ttatgaacat tattatagat ccaagtcaag atgggccaaa     360
gatgatgtgt tatccatgct ctctccttca tggaccagca ctctcgagca tgcttttctt     420
tggatcggtg ggtggcggcc ctctgtggct tttcacttgc tctactcaaa gtcaggtcat     480
cagtttgagg ctcaactcca tgagttgatt tgtgggttgg ggacaggtga cttgggtgac     540
ctttcagcta gtcaactcac ccgagttgat cagttacaga ggaagactgt cagggaagag     600
aacgagctga ctgagaagct tgcaaagcaa caagaaactg tagcagactc gtctatggtg     660
gagttagcac atgaggtgac tgagttgttg aggagcgaga acacgggtga tgaagtggag     720
gaagagcgag ttgagtcaac tctggcaccct aaaaaggatg gattgcagga aatcttgcag    780
atggctgatg atctacggct gagaactatc aaaggtgtta tcgagatttt gactccaatc     840
caagccgttc atttcttgat tgcagctgct gagttgcact tgcgccttca tgactggggc     900
aagaagggtg attgggcacg ccgcgtccac cactgatatg cgatttatta ggggataatc     960
atccatgaat tacacccata ttcgctgttc tgttgacata attaagaaat ggggagactg    1020
attttggttt tagaggcagg ataagcaaga tacgcagtaa tgtttaatta tattttcaga   1080
ttgaatctat ctatgtttac tatgtattat ccatcaggtg ctttgagtcc tcaagcactg   1140 gcatttagt ttaatatatg tattatgtat gatgttgcca gttaatttct ccaacttggc    1200
tttggctata attgaagtat tttgaaagat tgaa                                 1234

<210> SEQ ID NO 6
```

```
<211> LENGTH: 1083
<212> TYPE: DNA
<213> ORGANISM: Arabidopsis thaliana

<400> SEQUENCE: 6
gatagtctct atttatattg tagatatata aaccaactct ccatgatgag tactagcaaa      60
aatgggctag aaaatggcaa atcattccac aagtttttt gaatcatggc tcgttaaaca     120
aaatcaagat ttggatcagc ttgtacgtgc ctcaaaagac gacgacaaca acaacaagaa     180
caacaatgac atgatgttgt catctttaat tcatagtgtg gtgaaacatt atgaagaata     240
ttatagagag aaatcacgat acgctattag tgatatttta ggcatgttgc acccctcatg     300
gttaagtaat cttgaagatg cattttatg gattggtgga tggagaccta gtatggcttt     360
tcatttgtta tactcaaaat caggtataca acttgaagct aatcttcatg agttaattag     420
aggatttaac acaaaagatt taggaaattt aagtggtaat caacttgtat taattgatga     480
gttacaacat aagacaataa gtgaagaaag aaagctaagt gaaaatttag ctaaagttca     540
agaaacttta gctgatgcat caatggttga attatcacat gttgtgagtg aattaatgag     600
ggatgatcaa ttagttgtta atgatgaaga ggaaaaaatt aagaaaaata ttagtaaaaa     660
agaggaaagt ttattggatt tgttgaaaaa agctgatgat ttaaggttaa gtacaattaa     720
agagattttg agaattttga catcaacaca aggtgttcat ttcttgattg ctgctgctga     780
acttcatttg aggattcatg aatggggtaa gaagaaagat gctgctgttt ctcatcataa     840
atggtcatgt caaacaataa acgacgagcc aaattctgag gggacgtctg tcagaaatta     900
gtcattcaga tctattagaa tgatacagag aagatcaacg tggtacttaa tagttatgaa     960
tattcttaat tactacttaa ggagctagcc aaatgttatt agtattaatt actaggtaga    1020
ttgtaatagg ataaagttct tttaagggct ttttttttg tttcattttt gtttatgtag    1080
tga                                                                  1083
```

GENERATION OF PLANTS WITH ALTERED OIL CONTENT

REFERENCE TO RELATED APPLICATIONS

This is the § 371 U.S. National Stage of International Application No. PCT/US2004/012278, filed on Apr. 19, 2004, which was published in English under PCT Article 21(2), and which in turn claims the benefit of U.S. provisional patent application No. 60/464,558, filed Apr. 22, 2003, both of which are hereby incorporated by reference.

BACKROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the US soybean crop is crushed by the soy processing industry. Soy processing yields purified oil, which is sold at high value, while the remainder is sold principally for lower value livestock feed. (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from ~3.5% to ~7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990; James and Dooner, 1990). T-DNA mutagenesis screens (eldmann et al., 1989) that detected altered fatty acid composition identified the omega 3 desaturase (FAD3) and delta-12 desaturase (FAD2) genes (U.S. Pat. No. 5,952,544; Yadav et al., 1993; Okuley et al., 1994). A screen which focused on oil content rather than oil quality, analyzed chemically-induced mutants for wrinkled seeds or altered seed density, from which altered seed oil content was inferred Docks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992; Weigel D et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, Schaffer et al., 1998, Fridborg et al., 1999; Kardailsky et al., 1999; Christensen S et al., 1998).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO103.1 polypeptide. In preferred embodiments, the transgenic plant is selected from the group consisting of rapeseed, soy, corn, sunflower, cotton, cocoa, safflower, oil palm, coconut palm, flax, castor and peanut.

The invention further provides a method of producing oil comprising growing the transgenic plant and recovering oil from said plant.

The transgenic plant of the invention, is produced by a method that comprises introducing into progenitor cells of the plant a plant transformation vector comprising a nucleotide sequence that encodes or is complementary to a sequence that encodes a HIO103.1 polypeptide, and growing the transformed progenitor cells to produce a transgenic plant, wherein the HIO103.1 polynucleotide sequence is expressed causing the high oil phenotype.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the, class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Altered Oil Content Phenotype

We used an *Arabidopsis* activation tagging screen to identify the association between the gene we have designated "HIO103.1," (At1g09950; GI#18391091) encoding a nuclear protein (also know as F21M12.34, GI#15218335), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al, 2000). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC) analysis was performed to determine fatty acid content and composition of seed samples.

An *Arabidopsis* line that showed a high-oil phenotype was identified wherein oil content (i.e., fatty acids) constituted approximately 39.0% relative to a planting day average oil content of 35.0% (111% of PDA). The association of the HIO103.1 gene with the high oil phenotype was discovered by analysis of the genomic DNA sequence flanking the T-DNA insertion in the identified line. Accordingly, HIO103.1 genes and/or polypeptides may be employed in the development of genetically modified plants having a modified oil content phenotype ("a HIO103.1 phenotype"). HIO103.1 genes may be used in the generation of oilseed crops that provide improved oil yield from oilseed processing and in the generation of feed grain crops that provide increased energy for animal feeding. HIO103.1 genes may further be used to increase the oil content of specialty oil crops, in order to augment yield of desired unusual fatty acids. Transgenic plants that have been genetically modified to express HIO103.1 can be used in the production of oil, wherein the transgenic plants are grown, and oil is obtained from plant parts (e.g. seed) using standard methods.

HIO103.1 Nucleic Acids and Polypeptides

*Arabidopsis* HIO103.1 nucleic acid (genomic DNA) sequence is provided in SEQ ID NO:1 and in Genbank entry GI#18391091. The corresponding protein sequence is provided in SEQ ID NO:2 and in GI#15218335. Nucleic acids and/or proteins that are orthologs or paralogs of *Arabidopsis* HIO103.1, are described in Example 3 below.

As used herein, the term "HIO103.1 polypeptide" refers to a full-length HIO103.1 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO103.1 polypeptide causes an altered oil content phenotype when mis-expressed in a plant. In a further preferred embodiment, mis-expression of the HIO103.1 polypeptide causes a high oil phenotype in a plant. In another embodiment, a functionally active HIO103.1 polypeptide is capable of rescuing defective (including deficient) endogenous HIO103.1 activity when expressed in a plant or in plant cells; the rescuing polypeptide may be from the same or from a different species as that with defective activity. In another embodiment, a functionally active fragment of a full length HIO103.1 polypeptide (i.e., a native polypeptide having the sequence of SEQ ID NO:2 or a naturally occurring ortholog thereof) retains one of more of the biological properties associated with the full-length HIO103.1 polypeptide, such as signaling activity, binding activity, catalytic activity, or cellular or extra-cellular localizing activity. A HIO103. 1 fragment preferably comprises a HIO103.1 domain, such as a C— or N-terminal or catalytic domain, among others, and preferably comprises at least 10, preferably at least 20, more preferably at least 25, and most preferably at least 50 contiguous amino acids of a HIO103.1 protein. Functional domains can be identified using the PFAM program (Bateman A et al., 1999 Nucleic Acids Res 27:260-262; website at pfam.wustl.edu). Functionally active variants of full-length HIO103.1 polypeptides or fragments thereof include polypeptides with amino acid insertions, deletions, or substitutions that retain one of more of the biological properties associated with the full-length HIO103.1 polypeptide. In some cases, variants are generated that change the post-translational processing of a HIO103.1 polypeptide. For instance, variants may have altered protein transport or protein localization characteristics or altered protein half-life compared to the native polypeptide.

As used herein, the term "HIO103.1 nucleic acid" encompasses nucleic acids with the sequence provided in or complementary to the sequence provided in SEQ ID NO:1, as well as functionally active fragments, derivatives, or orthologs thereof. A HIO103.1 nucleic acid of this invention may be DNA, derived from genomic DNA or cDNA, or RNA.

In one embodiment, a functionally active HIO103.1 nucleic acid encodes or is complementary to a nucleic acid that encodes a functionally active HIO103.1 polypeptide. Included within this definition is genomic DNA that serves as a template for a primary RNA transcript (i.e., an mRNA precursor) that requires processing, such as splicing, before encoding the functionally active HIO103.1 polypeptide. A HIO103.1 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO103.1 polypeptide, or an intermediate form. A HIO103.1 polynucleotide can also include heterologous coding sequences, for example, sequences that encode a marker included to facilitate the purification of the fused polypeptide, or a transformation marker.

In another embodiment, a functionally active HIO103.1 nucleic acid is capable of being used in the generation of loss-of-function HIO103.1 phenotypes, for instance, via antisense suppression, co-suppression, etc.

In one preferred embodiment, a HIO103.1 nucleic acid used in the methods of this invention comprises a nucleic acid sequence that encodes or is complementary to a sequence that encodes a HIO103.1 polypeptide having at least 50%, 60%, 70%, 75%, 80%, 85%, 90%, 95% or more sequence identity to the polypeptide sequence presented in SEQ ID NO:2.

In another embodiment a HIO103.1 polypeptide of the invention comprises a polypeptide sequence with at least 50% or 60% identity to the HIO103.1 polypeptide sequence of SEQ ID NO:2, and may have at least 70%, 80%, 85%, 90% or 95% or more sequence identity to the HIO103.1 polypeptide sequence of SEQ ID NO:2. In another embodiment, a HIO103.1 polypeptide comprises a polypeptide sequence with at least 50%, 60%, 70%, 80%, 85%, 90% or 95% or more sequence identity to a functionally active fragment of the polypeptide presented in SEQ ID NO:2. In yet another embodiment, a HIO103.1 polypeptide comprises a polypeptide sequence with at least 50%, 60%, 70%, 80%, or 90% identity to the polypeptide sequence of SEQ ID NO:2 over its entire length.

In another aspect, a HIO103.1 polynucleotide sequence is at least 50% to 60% identical over its entire length to the HIO103.1 nucleic acid sequence presented as SEQ ID NO:1, or nucleic acid sequences that are complementary to such a HIO103.1 sequence, and may comprise at least 70%, 80%, 85%, 90% or 95% or more sequence identity to the HIO103.1 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO: 1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO103.1 polypeptide can be produced. For example, codons may be selected to increase the rate at which expression of the polypeptide occurs in a particular host species, in accordance with the optimum codon usage dictated by the particular host organism (see, e.g., Nakamura et al., 1999). Such sequence variants may be used in the methods of this invention.

The methods of the invention may use orthologs of the *Arabidopsis* HIO103.1. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis,* may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al., 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989; Dieffenbach and Dveksler, 1995). For instance, methods for generating a cDNA library from the plant species of interest and probing the library with partially homologous gene probes are described in Sambrook et al. A highly conserved portion of the *Arabidopsis* HIO103.1 coding sequence may be used as a probe. HIO103.1 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO103.1 polypeptides are used for ortholog isolation (see, e.g., Harlow and Lane, 1988, 1999). Western blot analysis can determine that a HIO103.1 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO103.1 nucleic acid and/or polypeptide sequences have been identified.

HIO103.1 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the invention involve incorporating the desired form of the HIO103.1 nucleic acid into a plant expression vector for transformation of in plant cells, and the HIO103.1 polypeptide is expressed in the host plant.

An isolated HIO103.1 nucleic acid molecule is other than in the form or setting in which it is found in nature and is identified and separated from least one contaminant nucleic acid molecule with which it is ordinarily associated in the natural source of the HIO103.1 nucleic acid. However, an isolated HIO103.1 nucleic acid molecule includes HIO103.1 nucleic acid molecules contained in cells that ordinarily express HIO103.1 where, for example, the nucleic acid molecule is in a chromosomal location different from that of natural cells.

Generation of Genetically Modified Plants with an Altered Oil Content Phenotype

HIO103.1 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO103.1 gene in a plant is used to generate plants with a high oil phenotype.

The methods described herein are generally applicable to all plants. Although activation tagging and gene identification is carried out in *Arabidopsis*, the HIO103.1 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. cainpestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as-a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO103.1 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower (Everett et al., 1987), and soybean (Christou et al., 1989; Kline et al., 1987).

Expression (including transcription and translation) of HIO103.1 may be regulated with respect to the level of expression, the tissue type(s) where expression takes place and/or developmental stage of expression. A number of heterologous regulatory sequences (e.g., promoters and enhancers) are available for controlling the expression of a HIO103.1 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, 1992), the CsVMV promoter (Verdaguer B et al., 1998) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993).

In one preferred embodiment, HIO103.1 expression is under control of regulatory sequences from genes whose expression is associated with early seed and/or embryo development. Legume genes whose promoters are associated with early seed and embryo development include *V. faba legumin* (Baumlein et al., 1991, Mol Gen Genet 225:121-8; Baumlein et al., 1992, Plant J 2:233-9), *V. faba usp* (Fiedler et al., 1993, Plant Mol Biol 22:669-79), pea *convicilin* (Bown et al., 1988, Biochem J 251:717-26), pea *lectin* (dePater et al., 1993, Plant Cell 5:877-86), *P. vulgaris beta phaseolin* (Bustos et al., 1991, EMBO 3 10:1469-79), *P. vulgaris* DLEC2 and PHS [beta] (Bobb et al., 1997, Nucleic Acids Res 25:641-7), and soybean beta-*Conglycinin*, 7S storage protein (Chamberland et al., 1992, Plant Mol Biol 19:937-49). Cereal genes whose promoters are associated with early seed and embryo development include rice *glutelin* ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice *prolamin* (Zhou & Fan, 1993, Transgenic Res 2:141-6), wheat *prolamin* (Hammond-Kosack et al., 1993, EMBO J 12:545-54), maize *zein* (Z4, Matzke et al., 1990, Plant Mol Biol 14:323-32), and barley *B-hordeins* (Entwistie et al., 1991, Plant Mol Biol 17:1217-31). Other genes whose promoters are associated with early seed and embryo development include oil palm GLO7A (7S globulin, Morcillo et al., 2001, Physiol Plant 112:233-243), *Brassica napus napin,* 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus oleosin* (Keddie et al., 1994, Plant Mol Biol 24:327-40), *Arabidopsis oleosin* (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:72941), and *Catharanthlus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952, 544). Alternative promoters are from plant storage protein genes (Bevan et al, 1993, Philos Trans R Soc Lond B Biol Sci 342:209-15).

In yet another aspect, in some cases it may be desirable to inhibit the expression of endogenous HIO103.1 in a host cell. Exemplary methods for practicing this aspect of the invention include, but are not limited to antisense suppression (Smith, et al.,1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., 1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous HIO103.1 that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO103.1-specific PCR is used to identify whether a mutated plant has a HIO103.1 mutation. Plants having HIO103.1 mutations may then be tested for altered oil content, or alternatively, plants maybe tested for altered oil content, and then HIO103.1-specific PCR is used to determine whether a plant having altered oil content has a mutated HIO103.1 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the HIO103.1 gene or orthologs of HIO103.1 that may confer altered oil content (see Bert et al., Theor Appl Genet. June 2003;107(1):181-9; and Lionneton et al, Genome. December 2002; 45(6):1203-15). Thus, in a further aspect of the invention, a HIO103.1 nucleic acid is used to identify whether a plant having altered oil content has a mutation in endogenous HIO103.1 or has a particular allele that causes altered oil content.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a HIO103.1 Phenotype by Transformation with an Activation Tagging Construct Mutants were generated using the activation tagging "ACTTAG" vector, pSKI015 (GI#6537289; Weigel D et al., 2000). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance.

T3 seed pools were analyzed by Near Infrared Spectroscopy (NIR) intact at time of harvest. NIR infrared spectra were captured using a Bruker 22 N/F. Bruker Software was used to estimate total seed oil and total seed protein content using data from NIR analysis and reference methods according to the manufacturers instructions. Oil contents predicted by our calibration (PDX Oil 3, Predicts Hexane Extracted Oil) were compared for 40,000 individual ACTTAG lines. To identify high oil lines the NIR oil result was compared to the mean oil result for all ACTTAG lines planted on the same day (Relative oil content). Subsequent to seed compositional analysis ACTTAG flanking sequence was determined. 22,000 lines with recovered flanking sequences were considered in this analysis. From 22,000 placed ACTTAG lines 819 (~4%) had high oil (defined as oil content of >=107% of the planting day average oil content). The genome coordinates in this subset of high oil ACTTAG lines was evaluated and lines having 2 or more independent ACTTAG insertions, also displaying high oil, were identified and the flanking sequence confirmed by PCR and sequencing.

Line W000130481 (IN040467) had a NIR determined oil content of 39.0% relative to a planting day average oil content of 35.0% (111% of PDA). Line W000151561 (IN053303) had a NIR determined oil content of 38.3% relative to a planting day average oil content of 34.4%.

Line W000130481 (IN040467) had a confirmed ACITAG insertion on Chromosome 1 at bp 3244182.

Line W000151561 (IN053303) had a confirmed ACTTAG insertion on Chromosome 1 at bp 3251749.

Based on the presence of an enhancer-containing T-DNA insert near this candidate gene in more than one independent mutant line showing a high oil phenotype, we concluded that the insert was linked with the trait. The actual insert number for these mutant lines was unknown.

Example 2

Characterization of the T-DNA Insertion in Plants Exhibiting the Altered Oil Content Phenotype.

We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from lines IN040467 and IN053303, and Southern blot analysis verified the genomic integration of the ACTTAG T-DNA and showed the presence of the T-DNA insertions in each of the transgenic lines.

Inverse PCR was used to recover genomic DNA flanking the T-DNA insertion, which was then subjected to sequence analysis using a basic BLASTN search and/or a search of the *Arabidopsis* Information Resource (TAIR) database (available at the *arabidopsis*.org website). For ACTTAG line IN040467, there was sequence identity to nucleotides 131064-131227 on Arabidopsis genome BAC clone F21M12 chromosome 1 (GI#2160155), placing the left border junction downstream from 131227 (GI#2160155). The opposite flank (predicted right border junction) of this insert was not determined. Left border of IN040467 T-DNA was ~2637 bp 5' of the translation start site.

For ACTTAG line IN053303, there was sequence identity to nucleotides 138824-139118 on *Arabidopsis* genome BAC clone F21M12 chromosome 1 (GI#2160155), placing the left border junction downstream from 138824 (GI#2160155). The opposite flank (predicted right border junction) of this insert was not determined. Left border IN053303 T-DNA was ~10204 bp 5' of the translation start site.

Example 3

Analysis of *Arabidopsis* HIO103.1 Sequence

Sequence analyses were performed with BLAST (Altschul et al., 1997, 3. Mol. Biol. 215:403410), PFAM (Bateman et al., 1999, Nucleic Acids Res 27:260-262), PSORT (Nakai K, and Horton P, 1999,Trends Biochem Sci 24:34-6), and/or CLUSTAL (Thompson J D et al, 1994, Nucleic Acids Res 22:4673-4680).

BLASTN against ESTs:
There are 5 *Arabidopsis* ESTs that match this sequence.
gi:19876633
gi:9785424
gi:9785476
gi:9785503
gi:19743182

There are lots of ESTs from diverse plant species showing similarity to At1g09950. If possible, ESTs contigs of each species were made. The top hit for each of the following species are listed below and included in the "Orthologue Table": *Triticum aestivum, Gossypium hirsutum, Zea mays, Glycine max, Populus tremula, Oryza sativa, Lycopersicon esculentum, Solanum tuberosum, Brassica napus*, and *Hordeum vulgare*.

1. One EST from wheat
>gi|21634 *T. aestivum* 1b-c38 gene for IBP-1b (leucine zipper type transcription factor)

2. One EST contig from cotton
No At1g09950 homolog identified

3. One EST contig from maize
The contigged sequence is presented as SEQ ID NO.:3 below.

4. One EST contig from soybean
The contigged sequence is presented as SEQ ID NO.:4 below.

5. One EST contig from poplars
The contigged sequence is presented as SEQ ID NO.:5 below.

6. One EST from rice
>gi|10423526|dbj|AU108122.1 |AU108122 AU108122 Rice callus *Oryza sativa* (japonica cultivar-group) cDNA clone C30623

7. One EST from tomato
>gi|4384471 EST247439 tomato ovary, TAMU *Lycopersicon esculentum* cDNA clone cLED18D7

8. One EST contig from potato
The contigged sequence is presented as SEQ ID NO.:6 below.

BLASTP against all.aa results:
The protein At1g09950 has a high degree of homology to other plant proteins known to function as transcription factors. The top 10 BLAST results are listed below and are included in the "Orthologue Table"

1. Itself (3 redundant entries)
>gi|15218335|ref|NP_172466.1| hypothetical protein; protein id: At1g09950.1 [*Arabidopsis thaliana*]
>gi|25372756|pir||H86233 hypothetical protein [imported]—*Arabidopsis thaliana* >gi|2160187|gb| AAB60750.1| Similar to *Nicotiana* tumor-related protein (gb|26453). [*Arabidopsis thaliana*]
Score=1092 (389.5 bits), Expect=5.2e-110, P=5.2e-110

2. At1g58330 from *Arabidopsis* (4 redundant entries)
>gi|18406255|ref|NP_564730.1| expressed protein; protein id: At1g58330.1, supported by cDNA: gi_6520153 [*Arabidopsis thaliana*]
>gi|25372755|pir||T52443 hypothetical protein ZW2 [imported]—*Arabidopsis thaliana* >gi|6520154|dbj| BAA87938.1|ZW2 [*Arabidopsis thaliana*]
>gi|8979941|gb|AAF82255.1|AC008051_6 Identical to gene ZW2 from *Arabidopsis thaliana* gb|AB028196
Score=632 (227.5 bits), Expect=2.9e-61, P=2.9e-61

3. At4g18650 from *Arabidopsis* (4 redundant entries)
>gi|15233970|ref|NP_193600.1| putative protein; protein id: At4g18650.1[*Arabidopsis thaliana*]>gi|7486277|pir|| T04857 hypothetical protein F28A21.60—*Arabidopsis thaliana*>gi|4539384|emb|CAB37450.1| putative protein [*Arabidopsis thaliana*]>gi|7268659|emb|CAB78867.1| putative protein [*Arabidopsis thaliana*]
Score=218 (81.8 bits), Expect=2.2e-17, P=2.2e-17

The following sequences are other redundant entries of At4g18650. However, they differ from the sequences listed above by a few nucleotides. This is likely to be the result of sequencing errors or of single nucleotide polymorphisms with little or no effect on activity.
>gi|28393021|gb|AAO41945.1| unknown protein [*Arabidopsis thaliana*]>gi|28827732|gb|AAO50710.1| unknown protein [*Arabidopsis thaliana*]
Score=218 (81.8 bits), Expect=2.2e-17, P=2.2e-17

4. A gene from *Oryza sativa* (japonica cultivar-group) (2 redundant entries)
>gi|15408613|dbj|BAB64034.1|P0552C05.19 [*Oryza sativa* (japonica cultivar-group)]>gi|21104797|dbj| BAB93383.1|OSJNBb0022N24.3 [*Oryza sativa* (japonica cultivar-group)]
Score=204 (76.9 bits), Expect=6.6e-16, P=6.6e-16

5. A tumor-related protein from *Nicotina*
>gi|688423|dbj|BAA05470.1| tumor-related protein [*Nicotiana glauca×Nicotiana langsdorffii*]
Score=177 (67.4 bits), Expect=6.7e-13, P=6.7e-13

6. At4g18690 from *Arabidopsis* (4 redundant entries)
>gi|15233979|ref|NP_193604.1| putative protein; protein id: At4g18690.1 [*Arabidopsis thaliana* ]>gi|7486266|pir|| T04861 hypothetical protein F28A21.100—*Arabidopsis thaliana* >gi|4539388|emb|CAB37454.1| putative protein [*Arabidopsis thaliana*]>gi|7268663|emb|CAB78871.1| putative protein [*Arabidopsis thaliana*]
Score=158 (60.7 bits), Expect=2.3e-10, P=2.3e-10

7. An unnamed protein from *Oryza sativa* (japonica cultivar-group) (2 redundant entries)
>gi|8570052|dbj|BAA96757.1| unnamed protein product [*Oryza sativa* (japonica cultivar-group)]>gi|9757677|dbj| BAB08196.1| ESTs AU057825(S21823),AU057072 (S21123) correspond to a region of the predicted gene. ~Similar to *Nicotiana glauca×Nicotiana langsdorffii* mRNA for tumor-related protein (D26453) [*Oryza sativa* (japonica cultivar-group)]
Score=155 (59.6 bits), Expect=8.9e-10, P=8.9e-10

8. At4g18660 from *Arabidopsis* (4 redundant entries)
>gi|15233972|ref|NP_193601.1| putative protein; protein id: At4g18660.1 [*Arabidopsis thaliana*]>gi|7486278|pir|| T04858 hypothetical protein F28A21.70—*Arabidopsis thaliana*>gi|4539385|emb|CAB37451.1| putative protein [*Arabidopsis thaliana*]>gi|7268660|emb|CAB78868.1| putative protein [*Arabidopsis thaliana*]
Score=129 (50.5 bits), Expect=3.1e-09, Sum P(2)=3.1e-09

9. Transcription factor HBP-1b from wheat (3 redundant entries)
>gi|122772|sp|P3923|HBPB_WHEAT Transcription factor HBP-1b
>gi|100809|pir||S15347 transcription factor HBP-1b—wheat >gi|21635|emb|CAA40102.1|HBP-1b [*Triticum aestivum*]

Score=151 (58.2 bits), Expect=1.1e-08, P=1.1e-08

10. An unnamed protein from *Oryza sativa* (japonica cultivar-group) (3 redundant entries)

>gi|6498432|dbj|BAA87835.1| unnamed protein product [*Oryza sativa* (japonica cultivar-group)]

>gi|11138060|dbj|BAB17733.1| putative transcription factor HBP-1b—wheat [*Oryza sativa* (japonica cultivar-group)]

>gi|13873003|dbj|BAB44107.1| putative transcription factor HBP-1b—wheat [*Oryza sativa* (japonica cultivar-group)]

Score=146 (56.5 bits), Expect=3.3e-08, P=3.3e-08

| Ortholog Gene Name | Species | >GI # | % ID to HIO103.1 | Score(s) (BLAST, Clustal, etc.) |
|---|---|---|---|---|
| A protein from rice | *Oryza sativa* (*japonica* cultivar-group) | >gi|15408613| >gi|21104797| | Length = 277 Identities = 64/205 (31%), Positives = 95/205 (46%) | BLASTP Score = 204 (76.9 bits), Expect = 6.6e−16, P = 6.6e−16 |
| A tumor-related protein from Nicotina | *Nicotiana glauca* x *Nicotiana langsdorffii* | >gi|688423 | Length = 287 Identities = 63/241 (26%), Positives = 112/241 (46%) | BLASTP Score = 177 (67.4 bits), Expect = 6.7e−13, P = 6.7e−13 |
| An unnamed protein from rice | *Oryza sativa* (*japonica* cultivar-group) | >gi|8570052| >gi|9757677| | Length = 269 Identities = 67/232 (28%), Positives = 98/232 (42%) | BLASTP Score = 155 (59.6 bits), Expect = 8.9e−10, P = 8.9e−10 |
| HBP-1b transcription factor from wheat | *Triticum aestivum* | >gi|122772 >gi|100809 >gi|21635| | Length = 332 Identities = 51/200 (25%), Positives = 91/200 (45%) | BLASTP Score = 151 (58.2 bits), Expect = 1.1e−08, P = 1.1e−08 |
| An unnamed protein from rice | *Oryza sativa* (*japonica* cultivar-group) | >gi|6498432| >gi|11138060| >gi|13873003| | Length = 264 Identities = 50/201 (24%), Positives = 92/201 (45%) | BLASTP Score = 146 (56.5 bits), Expect = 3.3e−08, P = 3.3e−08 |
| One EST from wheat | *Triticum aestivum* | gi|21634 | Length = 2204 Identities = 51/200 (25%), Positives = 91/200 (45%), Frame = +2 | TLASTPN Score = 151 (58.2 bits), Expect = 7.1e−09, P = 7.1e−09 |
| One EST contig from maize | *Zea mays* | gi|422028 gi|422029 | Length = 1163 Identities = 51/201 (25%), Positives = 91/201 (45%), Frame = +1 | TLASTPN Score = 139 (54.0 bits), Expect = 7.6e−08, P = 7.6e−08 |
| One EST contig from soybean | *Glycine max* | gi|7685470 gi|22930307 | Length = 1022 Identities = 41/129 (31%), Positives = 67/129 (51%), Frame = +3 | TLASTPN Score = 169 (64.5 bits), Expect = 2.4e−12, P = 2.4e−12 |
| One EST contig from poplars | *Populus tremula* | gi|18004849 gi|24060736 gi|24063323 gi|24063961 gi|24061283 gi|24064370 gi|24061976 gi|24063658 gi|24065989 gi|24060893 gi|24061066 gi|24061169 gi|24062091 gi|24061232 gi|24064452 gi|24065387 gi|24064857 gi|24064628 gi|24063100 gi|24065142 gi|24062202 gi|24063141 | Length = 1250 Identities = 45/178 (25%), Positives = 79/178 (44%), Frame = +3 | TLASTPN Score = 109 (43.4 bits), Expect = 0.00036, P = 0.00036 |

| Ortholog Gene Name | Species | >GI # | % ID to HIO103.1 | Score(s) (BLAST, Clustal, etc.) |
|---|---|---|---|---|
| | | gi\|24066218 | | |
| | | gi\|24063168 | | |
| | | gi\|23979309 | | |
| | | gi\|23979991 | | |
| | | gi\|23979824 | | |
| | | gi\|22552422 | | |
| | | gi\|24016600 | | |
| | | gi\|24049533 | | |
| | | gi\|24050145 | | |
| | | gi\|24056785 | | |
| | | gi\|24048644 | | |
| One EST from rice | *Oryza sativa* (*japonica* cultivar-group) | >gi\|10423526 | Length = 759 Identities = 39/160 (24%), Positives = 67/160 (41%), Frame = +3 | TLASTPN Score = 98 (39.6 bits), Expect = 0.70, P = 0.51 |
| One EST from tomato | *Lycopersicon esculentum* | gi\|4384471 | Length = 608 Identities = 53/209 (25%), Positives = 105/209 (50%), Frame = +3 | TLASTPN Score = 193 (73.0 bits), Expect = 2.2e−15, P = 2.2e−15 |
| One EST contig from potato | *Solanum tuberosum* | gi\|21376875 gi\|21376876 gi\|18256330 | Length = 1083 Identities = 27/96 (28%), Positives = 48/96 (50%), Frame = +2 | TLASTPN Score = 124 (48.7 bits), Expect = 1.6e−12, Sum P(2) = 1.6e−12 |

Closest *Arabidopsis* Homologs:

| | | | | |
|---|---|---|---|---|
| At1g58330 | *Arabidopsis thaliana* | >gi\|18406255 >gi\|25372755 >gi\|6520154 >gi\|8979941 | Length = 225 Identities = 121/213 (56%), Positives = 162/213 (76%) | BLASTP Score = 632 (227.5 bits), Expect = 2.9e−61, P = 2.9e−61 |
| At4g18650 | *Arabidopsis thaliana* | >gi\|15233970 >gi\|7486277 >gi\|4539384 >gi\|7268659 | Length = 229 Identities = 58/209 (27%), Positives = 107/209 (51%) | BLASTP Score = 218 (81.8 bits), Expect = 2.2e−17, P = 2.2e−17 |
| At4g18690 | *Arabidopsis thaliana* | >gi\|15233979 >gi\|7486266\| >gi\|4539388 >gi\|7268663\| | Length = 368 Identities = 54/194 (27%), Positives = 99/194 (51%) | BLASTP Score = 158 (60.7 bits), Expect = 2.3e−10, P = 2.3e−10 |
| At4g18660 | *Arabidopsis thaliana* | >gi\|15233972\| >gi\|7486278\| >gi\|4539385\| >gi\|7268660\| | Length = 281 Identities = 34/105 (32%), Positives = 57/105 (54%) | BLASTP Score = 129 (50.5 bits), Expect = 3.1e−09, Sum P(2) = 3.1e−09 |

At1g09950 is a non-secretory protein and lacks signal peptide (signalP). No transmembrane domain was detected for At1g09950 by TMHMM. At1g09950 is likely to be localized to the nucleus (40% nuclear, 28% cytoplasmic, 16% rnitochondrial by PSORT2). Pfam analysis showed that At1g09950 has limited homology to known protein domains.

The fact that At1g09950 is likely to be a nuclear protein and that it has low degree of homology to known transcription factors outside their DNA binding domain, it can likely be concluded that At1g09950 regulates gene expression in the nucleus.

Example 4

Generation of Mutated Plants with a HIO103.1 Phenotype

The invention further provides a method of identifying plants that have mutations in, or an allele of, endogenous HIO103.1 that confer a HIO103.1 phenotype, and generating progeny of these plants that also have the HIO103.1 phenotype and are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO103.1-specific PCR is used to identify whether a mutated plant has a HIO103.1 mutation. Plants having HIO103.1 mutations may then be tested for the HIO103.1 phenotype, or alternatively, plants may be tested for the HIO103.1 phenotype, and then HIO103.1-specific PCR is used to determine whether a plant having the HIO103.1 phenotype has a mutated HIO103.1 gene. TILLING can identify mutations that may alter the expression of specific genes or the activity of proteins encoded by these genes (see Colbert et al. (2001) Plant Physiol 126:480484; McCallum et al. (2000) Nature Biotechnology 18:455-457).

In another method, a candidate gene/Quantitative Trait Locus (QTLs) approach can be used in a marker-assisted breeding program to identify alleles of or mutations in the HIP103.1 gene or orthologs of HIO103.1 that may confer the HIO103.1 phenotype (see Foolad et al., Theor Appl Genet. (2002) 104(6-7):945-958; Rothan et al., Theor Appl Genet (2002) 105(1):145-159; Dekkers and Hospital, Nat Rev Genet. January (2002);3(1):22-32).

Thus, in a further aspect of the invention, a HIO103.1 nucleic acid is used to identify whether a plant having a HIO103.1 phenotype has a mutation in endogenous HIO103.1 or has a particular allele that causes the HIO103.1 phenotype compared to plants lacking the mutation or allele, and generating progeny of the identified plant that have inherited the HIO103.1 mutation or allele and have the HIO103.1 phenotype.

Example 5

To confirm that over-expression of At1g09950 cause the high seed oil phenotype in HIO103.1, this gene was cloned into an over-expression vector behind the strong constitutive CsVMV promoter and transformed into *Arabidopsis* plants. The transformation vector contains the nptII gene which confers resistance to kanamycin as a selectable marker. Transformants in the Ti generation were selected by germinating seed on kanamycin-containing medium. Plants resistant to the antibiotic were transplanted to soil in 32 cell flats and grown to maturity. Wild-type non-transgenic Col-0 plants that were germinated on agar medium were transplanted into the same flat to serve as a control for the experiment. Seed was harvested from both transgenic and control plants and seed oil content estimated by NIR as described above. Seed from plants over-expressing At1g09950 from the CsVMV promoter have a higher oil content than seed from wild-type plants. Seed from plants over-expressing At1g09950 showed an increase in seed oil content of 7% (34.8% oil compared to 32.5% oil for the control) in the first experiment and an increase of 6% (35.6% oil compared to 33.5% for the control) in the second experiment. These results demonstrate that over-expression of At1g09950 causes an increase in seed oil content.

REFERENCES

Altschul, S. F. et al., J. Mol. Biol. 215:403-410, 1990.
Altschul, S. F. et al., Nucleic Acids Res. 25:3389-3402, 1997.
Ausubel F M et al., Current Protocols in Molecular Biology, John Wiley & Sons, New York, N.Y., 1993.
Baldwin D et al., Cur Opin Plant Biol. 2(2):96-103, 1999.
Bateman et al., 1999, Nucleic Acids Res 27:260-262 (website at pfam.wustl.edu).
Baulcombe D, Arch Virol Suppl 15:189-201, 1999.
Cannon et al., Plant Molec. Biol. (1990) 15:39-47.
Ch'ng et al., Proc. Natl. Acad. Sci. USA (1989) 86:10006-10010
Christensen S et al., 9th International Conference on *Arabidopsis* Research. Univ. of Wisconsin-Madison, Jun. 24-28, 1998. Abstract 165.
Christou et al., Proc. Natl. Acad. Sci USA (1989) 86:7500-7504.
Cough, S J and Bent, A F, the Plant Journal 16(6): 735-743, 1998.
De Block et al., Plant Physiol. (1989) 91:694-701.
Dieffenbach C and Dveksler G (Eds.) PCR Primer: A Laboratory Manual, Cold Spring Harbor Laboratory Press, NY, 1989.
Everett et al., Bio/Technology (1987) 5:1201
Peldmann et al., Science 243: 1351-1354, 1989.
Pocks N and Benning C, Plant Physiol 118:91-101, 1998.
Fridborg I et al., Plant Cell 11: 1019-1032, 1999.
Fujita, T et al., Plant J. 5:645-654, 1994.
Geest A H and Hall T C, Plant Mol Biol 32(4):579-88, 1996.
Gelvin, S. B., Schilperoort, R. A., Varma, D. P. S., eds. Plant Molecular Biology Manual 1990.
Glick, B R and Thompson, J E, Eds. Methods in Plant Molecular Biology and Biotechnology, p. 213-221, CRC Press, 1993.
Harlow E and Lane D, Antibodies: A Laboratory Manual, Cold Spring Harbor Laboratory Press, 1988, New York.
Harlow E and Lane D, Using Antibodies: A Laboratory Manual, Cold Spring Harbor Laboratory Press, 1999, New York
Hayashi H et al., Science 258: 1350-1353, 1992.
Jako et al., Plant Physiology 126(2):861-74, 2001.
James D W and Dooner H K (1990) Theor Appl Genet 80, 241-245.
Jensen, L. G., et al., Proc. Natl. Acad. Sci. USA 93:3487-3491, 1996.
Jones J D et al., Transgenic Res 1:285-297 1992.
Kardailsky l et al., Science 286: 1962-1965, 1999.
Katavic V. et al., Plant Physiology 108(1):399409, 1995.
Kline et al., Nature (1987) 327:70.
Kunkel T A et al., Methods Enzymol. 204:125-39, 1991.
Lemieux B., et al., 1990, Theor Appl Genet 80, 234-240.
Nakamura Y. et al., 1999, Nucleic Acids Res 27:292.
Napoli, et al., Plant Cell 2:279-289, 1990.
Okuley et al., Plant Cell 6(1):147-158, 1994.
Omirulleh et al., Plant Mol Biol. 21(3):415-28, 1993.
Sambrook et al., Molecular Cloning: A Laboratory Manual (Second Edition), Cold
Sasaki, T., Nature 420:312-316, 2002.
Spring Harbor Press, Plainview, N.Y., 1989.
Schaffer R, et al., Cell 93: 1219-1229, 1998.
Sheehy et al., Proc. Natl. Acad. Sci. USA (1988) 85:8805-8809.
Smith, et al., Nature 334:724-726, 1988.
Smith et al., Mol. Gen. Genetics (1990) 224:477-481.
Tabata, T. et al., EMBO J. 10:1459-1467, 1991.
Thompson J D et al., Nucleic Acids Res 22:4673-4680, 1994.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Waterhouse, et al., Proc. Natl. Acad. Sci. USA 95:13959-13964, 1998.
Weigel D, et al., Plant Physiology, 122:1003-1013, 2000.
Wilson K et al., Plant Cell 8: 659-671, 1996.
Yadav N S et al., (1993) Plant Physiol 103, 467-476.

It is claimed:

1. A transgenic plant comprising a plant transformation vector comprising a nucleotide sequence that encodes a HIO103.1 polypeptide comprising:
   a) the amino acid sequence set forth as SEQ ID NO: 2; or
   b) an amino acid sequence having at least 95% sequence identity to the amino acid sequence of SEQ ID NO: 2;
   whereby the transgenic plant has a higher oil content relative to a plant of the same species that does not comprise the plant transformation vector.

2. The transgenic plant of claim 1, which is selected from the group consisting of rapeseed, soy, corn, sunflower, cotton, cocoa, safflower, oil palm, coconut palm, flax, castor and peanut.

3. A plant part obtained from the plant according to claim 1.

4. The plant part of claim 3, which is a seed.

5. A method of producing oil comprising growing the transgenic plant of claim 1 and recovering oil from said plant.

6. A method of producing a high oil phenotype in a plant, said method comprising: a) introducing into progenitor cells of the plant a plant transformation vector comprising a nucleotide sequence that encodes a HIO103.1 polypeptide comprising the amino acid sequence set forth as SEQ ID NO: 2; or an amino acid sequence having at least 95% sequence identity to the amino acid sequence of SEQ ID NO: 2; and b) growing the transformed progenitor cells to produce a transgenic plant,
   wherein said nucleotide sequence is expressed, and said transgenic plant exhibits a higher oil content relative to a plant of the same species that does not comprise the plant transformation vector, thereby producing a high oil phenotype.

7. A plant obtained by a method of claim 6.

8. The plant of claim 7, which is selected from the group consisting of rapeseed, soy, corn, sunflower, cotton, cocoa, safflower, oil palm, coconut palm, flax, castor and peanut.

9. The transgenic plant of claim 1, wherein the nucleotide sequence encodes a HIO103.1 polypeptide comprising an amino acid sequence having at least 95% sequence identity to the amino acid sequence of SEQ ID NO: 2.

10. The transgenic plant of claim 9, wherein the nucleotide sequence encodes a HIO103.1 polypeptide comprising the amino acid sequence set forth as SEQ ID NO: 2.

11. The transgenic plant of claim 10, wherein the nucleotide sequence that encodes a HIO103.1 polypeptide consists of the amino acid sequence set forth as SEQ ID NO: 2.

12. The method of claim 6, wherein the nucleotide sequence encodes a HIO103.1 polypeptide comprising an amino acid sequence having at least 95% sequence identity to the amino acid sequence of SEQ ID NO: 2.

13. The method of claim 12, wherein the nucleotide sequence encodes a HIO103.1 polypeptide comprising the amino acid sequence set forth as SEQ ID NO: 2.

14. The method of claim 13, wherein the nucleotide sequence that encodes a HIO103.1 polypeptide consists of the amino acid sequence set forth as SEQ ID NO: 2.

* * * * *